(12) United States Patent
Wu

(10) Patent No.: US 6,669,672 B2
(45) Date of Patent: Dec. 30, 2003

(54) ONE-HANDED HYPODERMIC SYRINGE

(76) Inventor: Wen Ying Wu, No. 28, Shin-Shing Rd., Chung-Li, Tao-Yuan (TW)

( * ) Notice: Subject to any disclaimer, the term of this patent is extended or adjusted under 35 U.S.C. 154(b) by 0 days.

(21) Appl. No.: 10/074,458

(22) Filed: Feb. 11, 2002

(65) Prior Publication Data

US 2002/0183788 A1 Dec. 5, 2002

(30) Foreign Application Priority Data

Jun. 4, 2001 (TW) .................................. 90209147 U

(51) Int. Cl.[7] .............................................. A61M 5/315
(52) U.S. Cl. ...................................... 604/220; 604/227
(58) Field of Search ................................. 604/227, 187, 604/181, 218, 220, 235, 15; D24/114

(56) References Cited

U.S. PATENT DOCUMENTS

| 3,930,499 | A | * | 1/1976 | Rimbaud | ................... 604/197 |
|---|---|---|---|---|---|
| 5,531,691 | A | * | 7/1996 | Shonfeld et al. | ............ 604/110 |
| 5,902,278 | A | * | 5/1999 | Aguilar | ...................... 604/227 |
| 6,126,643 | A | * | 10/2000 | Vaillancouert | .............. 604/218 |
| 6,413,236 | B1 | * | 7/2002 | Van Dyke | ................... 604/110 |

* cited by examiner

Primary Examiner—Michael J. Hayes
Assistant Examiner—Lina R Kentos
(74) Attorney, Agent, or Firm—Alan Kamrath; Rider Bennett, LLP

(57) ABSTRACT

A one-handed hypodermic syringe is a renovated structure that allows users to push and pull the syringe by one hand. The medical personnel may place their thumbs inside the ring disposed in the distal end of the plunger and may press the concave objects disposed in the distal end of the barrel by their index fingers and middle fingers. Thus, the syringe may be held steadily, and the pull-push action of the injection manipulated with one band. The convenience for the medical personnel's use of hypodermic syringe is thereby enhanced.

7 Claims, 5 Drawing Sheets

ONE-HANDED HYPODERMIC SYRINGE

BACKGROUND OF THE INVENTION

1. Field of the Invention

The present invention relates to a one-handed hypodermic syringe comprising two concave objects opposite to each other on the rear portion of the syringe as well as a ring with a broken slit on the distal portion of the plunger of the syringe. The medical personnel can hold the ring steadily with their thumbs, and the syringe with their index fingers and middle fingers, to manipulate the pull-push action of the injection.

Secondly, the present invention consists of a blocking-object inside the distal end of the syringe to prevent the plunger from moving out of the barrel chamber, thereby keeping the syringe needle inside the syringe in consideration of safety.

Thirdly, there is a slit near the distal end of the plunger. In the event the medical personnel pulls the plunger with excessive force, their thumbs can be released from the slit so as to prevent the plunger from falling out of the syringe and keeping the needle inside the syringe barrel for safety consideration.

2. Description of the Prior Art

The present invention relates to a one-handed hypodermic syringe designed to improve the performance of conventional syringes and of safety syringes.

SUMMARY OF THE INVENTION

The conventional syringes are subject to the restrictions as follows:

1. Users need to keep the syringe needle facing upward and pull the plunger outward slightly before the injection. The plunger is then pushed inward so as to remove the air out of the syringe. This motion requires two bands.

2. To use the syringes equipped with the safety needle, users have to pull the plunger outward after the injection in order to force the syringe needle to return to its original position inside the barrel. Two hands are required in this motion, also.

Apparently, medical personnel always need to use two hands for the injection. However, the medical personnel have to use one hand occasionally. Therefore, both medical personnel and patients face certain level of risks.

In an effort to upgrade the performance of the hypodermic syringes, the inventor has studied the structure of syringes thoroughly so as to allow the medical personnel to use the syringes with one hand only.

The present invention will be apparent in its contents of technique after reading the detailed description of the preferred embodiments of the present invention in reference to the accompanying drawings, wherein:

DETAILED DESCRIPTION OF THE PREFERRED EMBODIMENT

Figure 1:
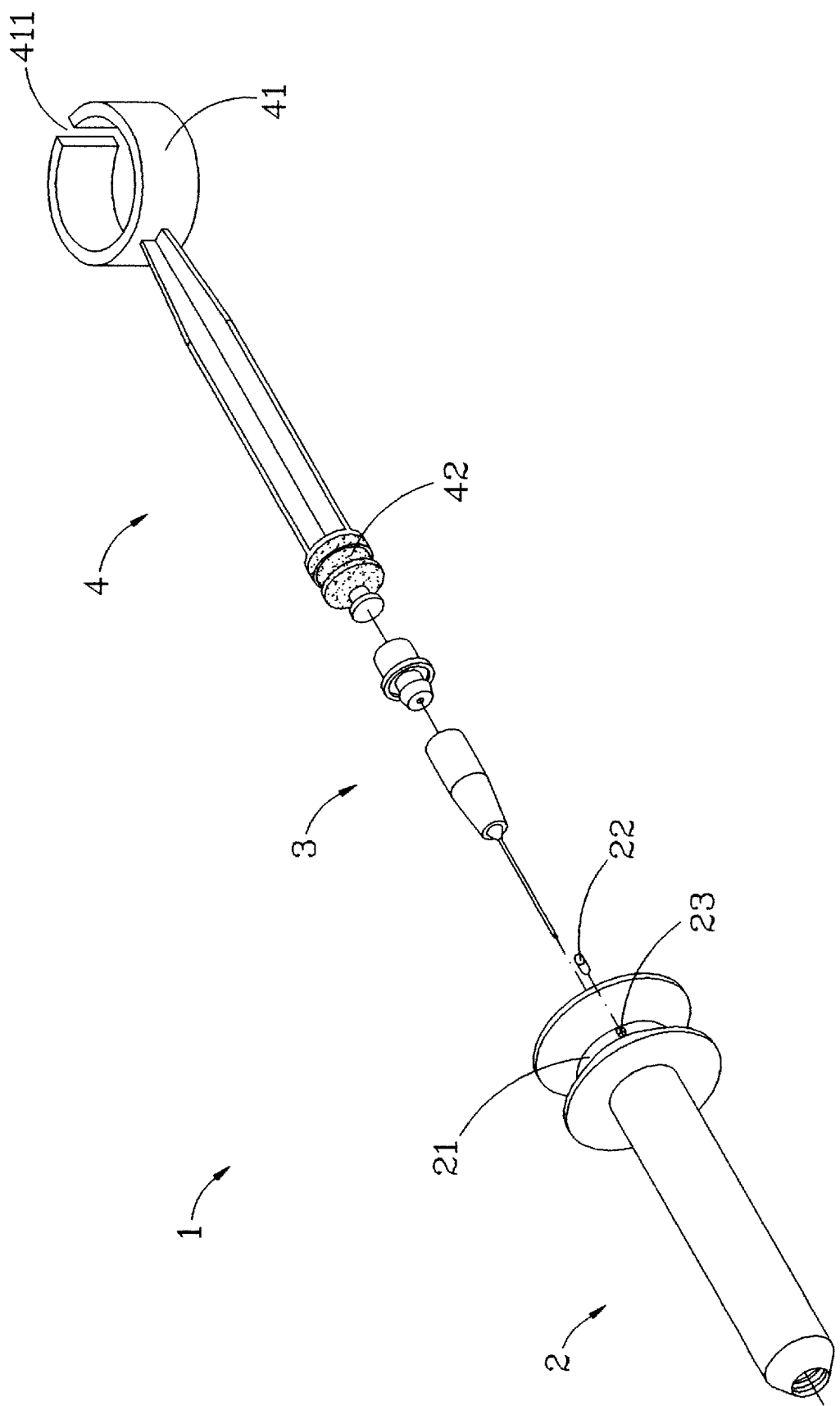
FIG. 1 is an exploded perspective view of the present invention.
Figure 2:
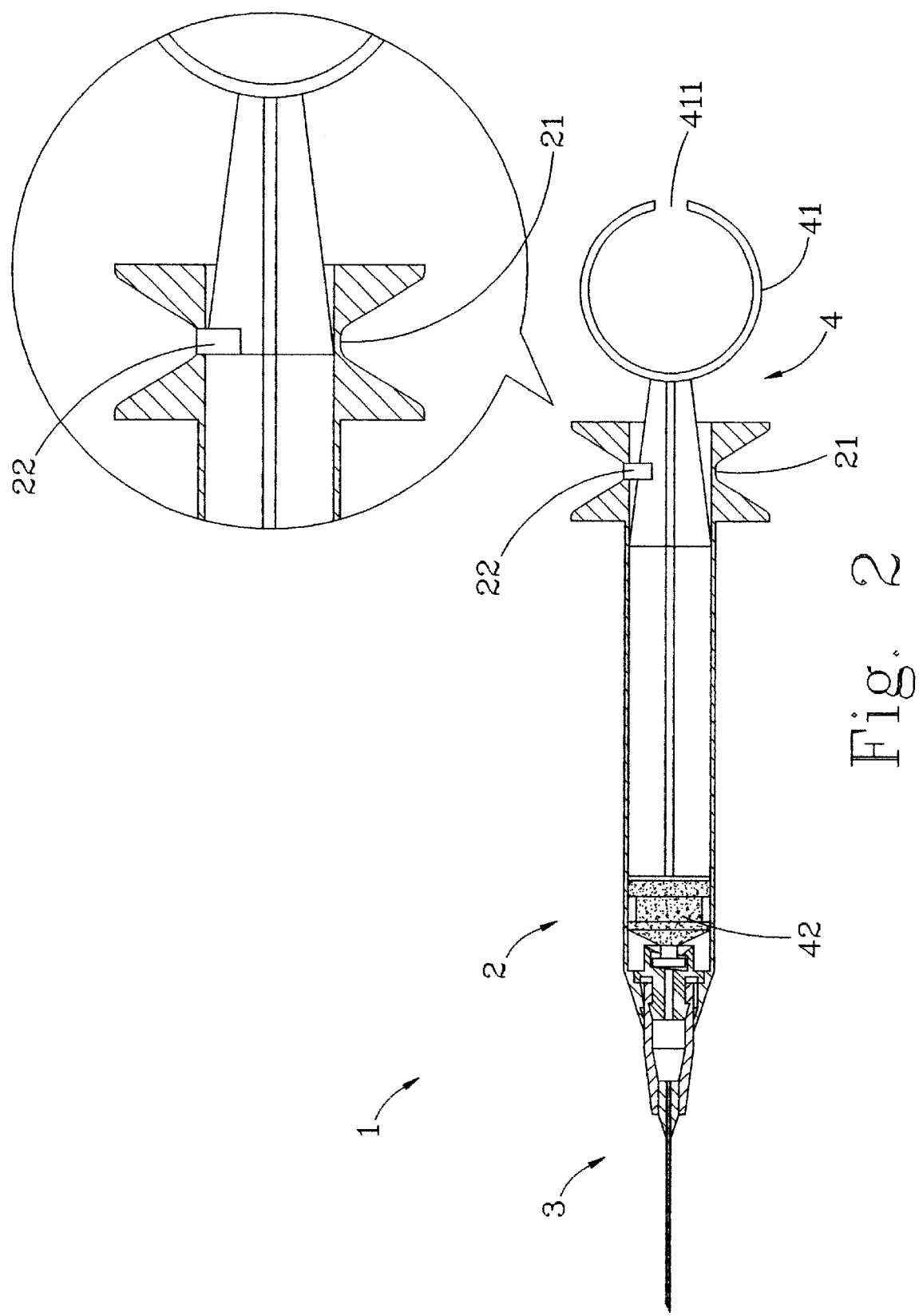
FIG. 2 is a sectional view of the present invention.
Figure 3:
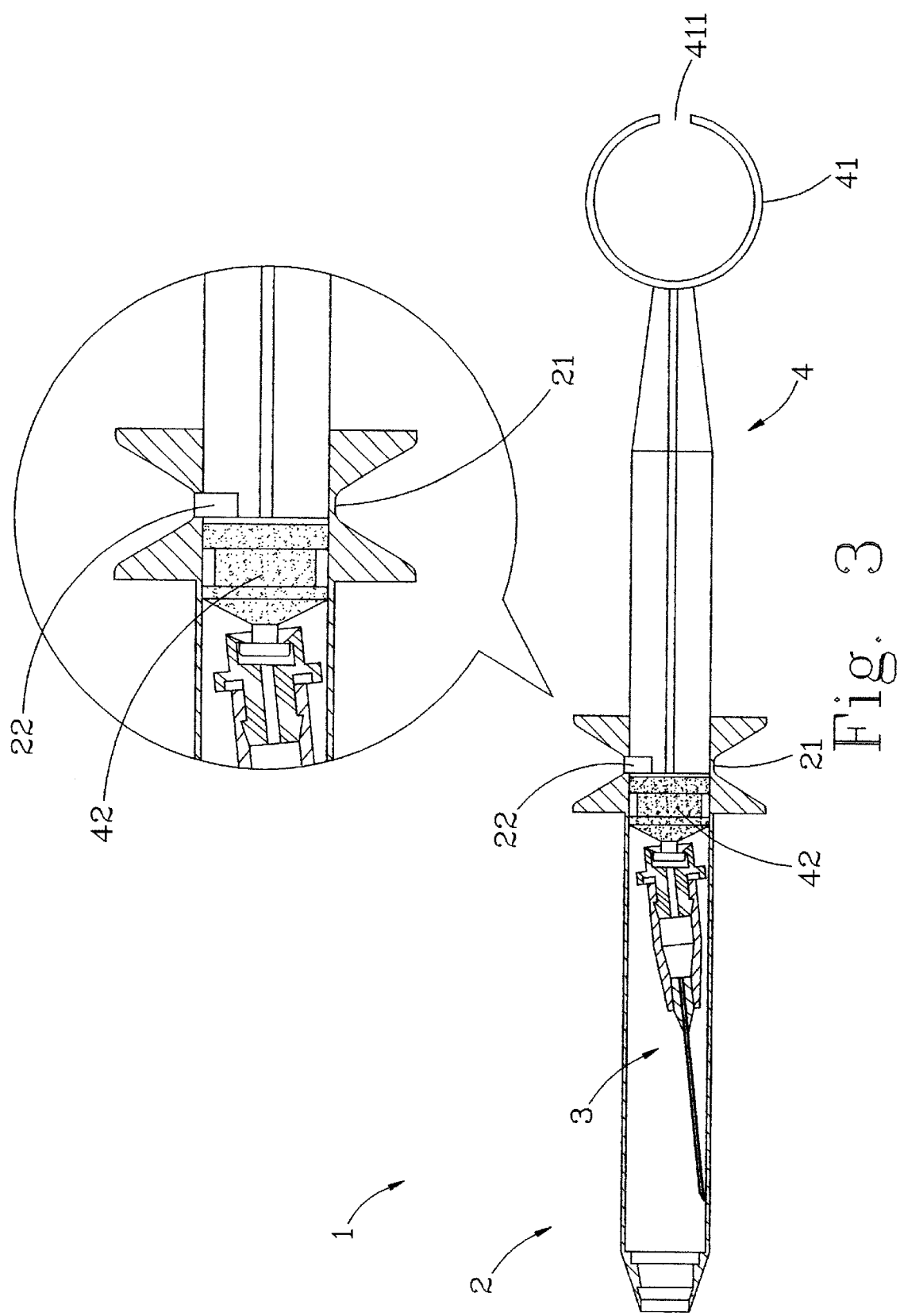
FIG. 3 is another sectional view of the present invention.

As shown by FIG. 1, FIG. 2, and FIG. 3, the syringe 1 consists of a barrel 2, a syringe needle 3, and a plunger 4. The syringe needle 3 is disposed in the front area of the barrel 2, and the plunger 4 is disposed inside the barrel 2.

There are two concave objects 21 disposed in the distal portion of the barrel 2 opposite to each other. Users may press the concave objects 21 with their fingers.

There is a ring 41 disposed in the distal end of the plunger 4. The ring 41 accommodates the user's thumbs 51.

Figure 4:
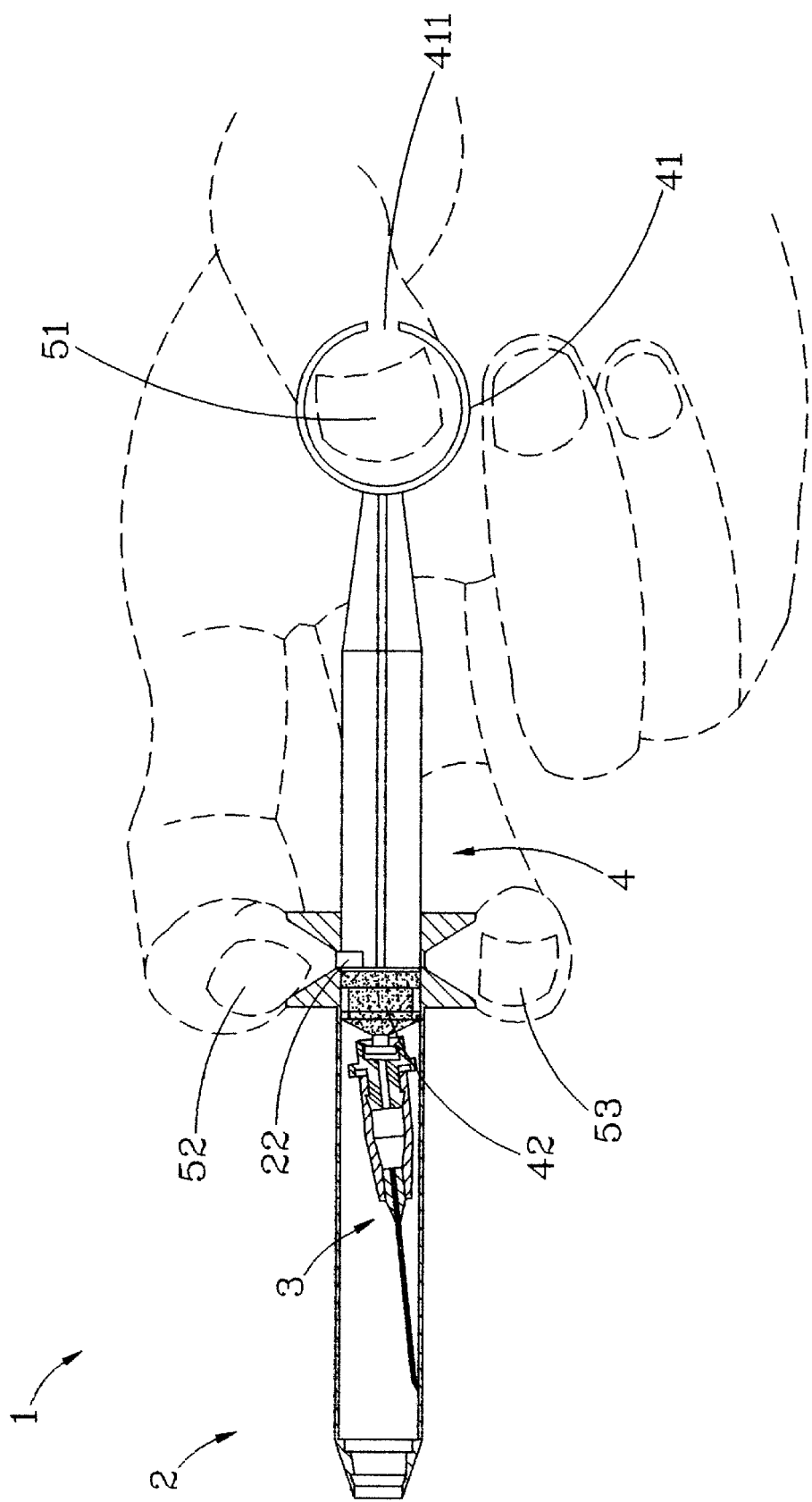
FIG. 4 is a view showing the motion of the present invention.

As shown by FIG. 4, the medical personnel can place their thumbs 51 through the ring 41, while their index fingers 52 and middle fingers 53 hold the concave objects 21 of the barrel 2 at the same time. Thus, the medical personnel can bold the syringe 1 steadily and push and pull the plunger 4 with one band.

To prevent the plunger 4 from moving out of the barrel 2 due to the user's excessive force pulling the plunger 4, a broken slit 23 is disposed in the distal end of the barrel 2. There is a stopper 22 disposed inside the broken slit 23 through the barrel 2. The stopper 22 presses the stuffing object 42 of the plunger 4 to prevent the plunger 4 from falling out of the barrel 2.

Figure 5:
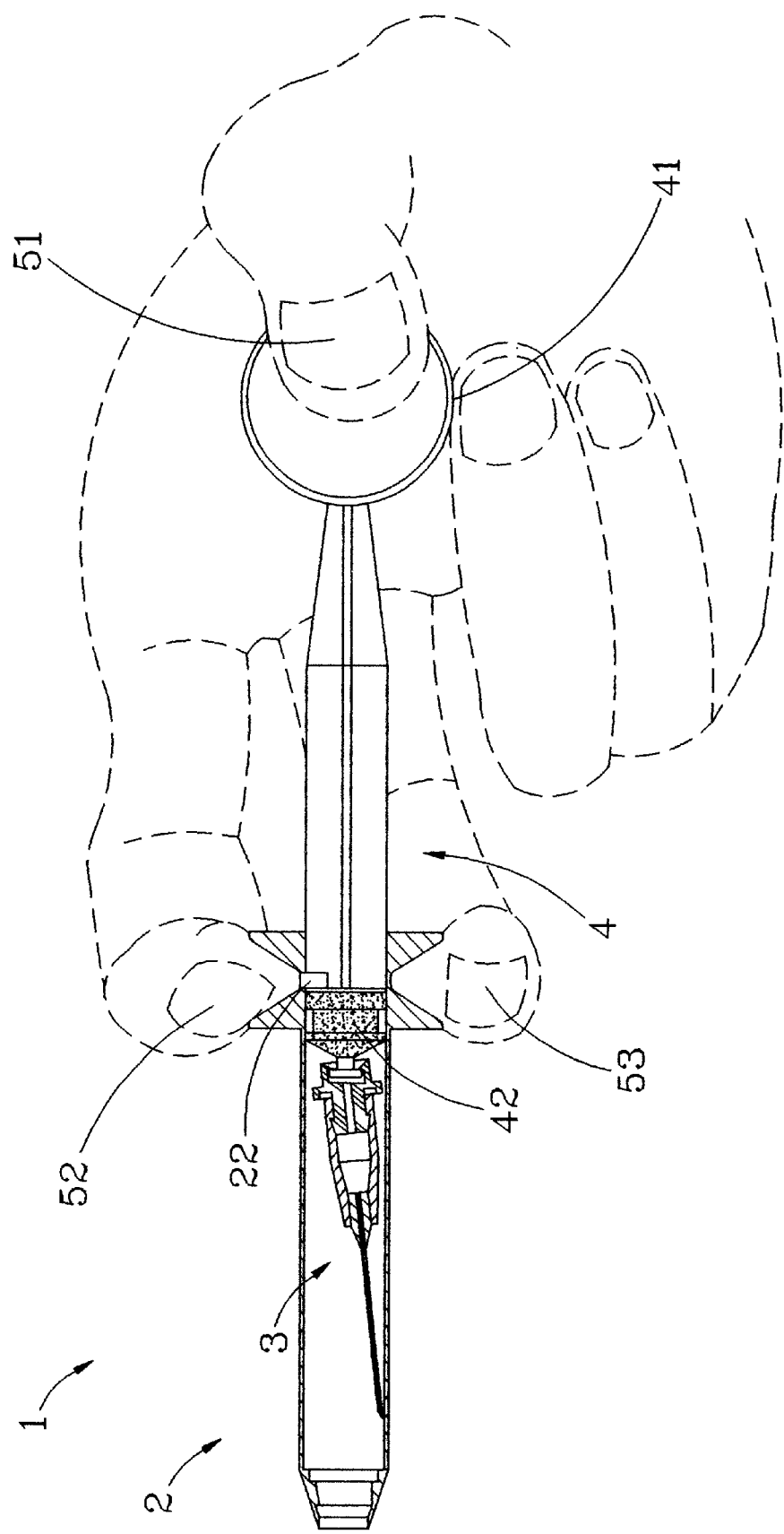
FIG. 5 is another view showing the motion of the present invention.

There is a slit 411 disposed in the ring 41 at the distal end of the plunger 4. In the event the thumb 51 presses the plunger 4 with excessive force, the thumb 51 falls out of the slit 411 as shown by FIG. 5 to prevent the plunger 4 from moving out of the barrel 2. Thus, the syringe needle 3 is kept inside the barrel for safety purposes.

The present invention can be installed in the conventional syringe. When installed in the safety syringe, the advantages of the present invention become more apparent.

Having thus described the invention, what the inventor hereby claims as new and desires to be secured by US Patent & Trademark Office includes:

What is claim is:

1. A one-handed hypodermic syringe comprising, in combination:

a barrel, with the barrel having a front end and a distal end, with objects disposed on the distal end of the barrel to accommodate users' fingers pressing the barrel;

a syringe needle, with the syringe needle disposed on the front end of the barrel;

a plunger inside the barrel, with a ring disposed on a distal end of the plunger to allow users to place their fingers inside, wherein a broken sift is disposed in the distal end of the barrel; and a stopper separately formed from the barrel and received inside the broken slit to block the plunger and prevent the plunger from falling out of the barrel when being pulled from the barrel.

2. A one-handed hypodermic syringe as stated in claim 1, wherein a slit is disposed in the ring of the plunger, with the slit dividing the ring into first and second halves each having a free end opposite to the plunger, wit the free ends being spaced to define a gap between the free ends through which fingers placed in the ring can escape when the ring is pressed with excessive force.

3. The one-handed hypodermic syringe as stated in claim 2, with the plunger including a stuffing object, with the stopper received inside the broken slit blocking the stuffing object.

4. A one-banded hypodermic syringe as stated in claim 1, with the objects being concave and disposed on the barrel opposite to each other.

5. A one-handed hypodermic syringe as stated in claim 4, the syringe needle is a retrievable safety needle.

6. A one-handed hypodermic syringe as stated in claim 4, wherein a slit is disposed in the ring of the plunger, with the slit dividing the ring into first and second halves each having a free end opposite to the plunger, with the free ends being spaced to define a gap between the free ends through which fingers placed in the ring can escape when the ring is pressed with excessive force.

7. The one-handed hypodermic syringe as stated in claim 6, with the plunger including a stuffing object, with the stopper received inside the broken slit blocking the stuffing object.

\* \* \* \* \*